US011039835B2

(12) United States Patent
Wixey et al.

(10) Patent No.: US 11,039,835 B2
(45) Date of Patent: Jun. 22, 2021

(54) MEDICAL DEVICE DRIVE SYSTEM

(71) Applicant: Intuitive Surgical Operations, Inc., Sunnyvale, CA (US)

(72) Inventors: Matthew A. Wixey, San Jose, CA (US); William A. Burbank, Sandy Hook, CT (US); Nicholas H. Ragosta, San Francisco, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 154 days.

(21) Appl. No.: 16/333,924

(22) PCT Filed: Sep. 8, 2017

(86) PCT No.: PCT/US2017/050710
§ 371 (c)(1),
(2) Date: Mar. 15, 2019

(87) PCT Pub. No.: WO2018/052806
PCT Pub. Date: Mar. 22, 2018

(65) Prior Publication Data
US 2019/0200983 A1    Jul. 4, 2019

Related U.S. Application Data

(60) Provisional application No. 62/395,360, filed on Sep. 15, 2016.

(51) Int. Cl.
*A61B 17/072* (2006.01)
*A61B 34/30* (2016.01)
(Continued)

(52) U.S. Cl.
CPC ...... *A61B 17/072* (2013.01); *A61B 17/07207* (2013.01); *A61B 34/30* (2016.02);
(Continued)

(58) Field of Classification Search
CPC ............ A61B 17/00234; A61B 17/072; A61B 17/07207; A61B 17/1114; A61B 17/068;
(Continued)

(56) References Cited

U.S. PATENT DOCUMENTS 4,207,898 A    6/1980  Becht
5,312,023 A *  5/1994  Green .............. A61B 17/07207
                                              227/175.1
(Continued)

FOREIGN PATENT DOCUMENTS

WO   WO-2013084221 A1   6/2013
WO   WO-2015153636 A1   10/2015
WO   WO-2015175200 A1   11/2015

OTHER PUBLICATIONS

International Search Report and Written Opinion for Application No. PCT/US2017/050710, dated Dec. 14, 2017, 12 pages.
(Continued)

*Primary Examiner* — Scott A Smith
(74) *Attorney, Agent, or Firm* — Schwegman Lundberg & Woessner, P.A.

(57) ABSTRACT

A medical device drive system including a lever body having portions defining a lever body cavity, a nut housing in the lever body cavity, and a first nut at least partially in the first nut cavity. The first nut is slideable in the first nut cavity between an engaged position in which the lead screw interface is engaged with the engagement portion of the lead screw, and a disengaged position in which the lead screw interface is not engaged with the engagement portion of the lead screw. The lead screw interface of the first nut is selectively engageable with the engagement portion of the lead screw by sliding the lever body and pin relative to the first nut housing.

15 Claims, 13 Drawing Sheets

(51) Int. Cl.
*A61B 34/35* (2016.01)
*F16H 25/24* (2006.01)
*A61B 17/00* (2006.01)
*A61B 17/068* (2006.01)
*A61B 17/11* (2006.01)
*A61B 34/00* (2016.01)
*F16H 25/20* (2006.01)

(52) U.S. Cl.
CPC ......... *A61B 34/35* (2016.02); *F16H 25/2454* (2013.01); *F16H 25/2472* (2013.01); *A61B 17/00234* (2013.01); *A61B 17/068* (2013.01); *A61B 17/1114* (2013.01); *A61B 34/70* (2016.02); *A61B 2017/00017* (2013.01); *A61B 2017/00022* (2013.01); *A61B 2017/00367* (2013.01); *A61B 2017/00398* (2013.01); *A61B 2017/00477* (2013.01); *A61B 2034/302* (2016.02); *F16H 2025/2065* (2013.01); *F16H 2025/2071* (2013.01)

(58) Field of Classification Search
CPC ......... A61B 34/20; A61B 34/30; A61B 34/35; A61B 34/37; A61B 34/70; A61B 34/71; A61B 2017/00398; A61B 2017/00477; A61B 2017/07214; A61B 2017/00017; A61B 2017/00022
USPC .............. 227/19, 175.1, 175.2, 176.1, 180.1; 606/1, 139, 205, 219
See application file for complete search history.

(56) References Cited

U.S. PATENT DOCUMENTS

| | | | |
|---|---|---|---|
| 5,382,885 A | | 1/1995 | Salcudean et al. |
| 5,609,601 A | | 3/1997 | Kolesa et al. |
| 5,779,130 A | * | 7/1998 | Alesi ................ A61B 17/07207 227/176.1 |
| 5,954,259 A | * | 9/1999 | Viola ................ A61B 17/07207 227/176.1 |
| 6,770,081 B1 | | 8/2004 | Cooper et al. |
| 7,485,127 B2 | * | 2/2009 | Nistal .................... A61B 5/061 606/180 |
| 7,543,516 B2 | | 6/2009 | Siefert |
| 7,780,651 B2 | | 8/2010 | Madhani et al. |
| 7,802,664 B2 | | 9/2010 | Hanna et al. |
| 7,918,230 B2 | * | 4/2011 | Whitman ............ A61B 17/068 128/898 |
| 7,984,663 B2 | | 7/2011 | Dent |
| 8,640,921 B2 | | 2/2014 | Meron et al. |
| 8,644,988 B2 | | 2/2014 | Prisco et al. |
| 8,968,312 B2 | | 3/2015 | Marczyk et al. |
| 9,060,860 B2 | | 6/2015 | Morris et al. |
| 9,549,818 B2 | | 1/2017 | Morrissey |
| 9,919,724 B2 | | 3/2018 | Lubischer et al. |
| 10,591,032 B2 | | 3/2020 | Wixey |
| 2003/0130677 A1 | * | 7/2003 | Whitman ............ A61B 17/072 606/167 |
| 2003/0216667 A1 | * | 11/2003 | Viola ................ A61B 10/0275 600/564 |
| 2007/0023477 A1 | * | 2/2007 | Whitman ............... A61B 34/71 227/175.1 |
| 2007/0270790 A1 | * | 11/2007 | Smith ................. A61B 17/1114 606/32 |
| 2008/0077159 A1 | * | 3/2008 | Madhani ................ A61B 34/37 606/130 |
| 2008/0177283 A1 | * | 7/2008 | Lee ........................ A61B 34/20 606/130 |
| 2008/0245842 A1 | | 10/2008 | Marczyk |
| 2008/0251568 A1 | * | 10/2008 | Zemlok ................ A61B 17/072 227/175.1 |
| 2008/0308603 A1 | * | 12/2008 | Shelton ............ A61B 17/07207 227/175.1 |
| 2009/0090764 A1 | * | 4/2009 | Viola ............... A61B 17/07207 227/176.1 |
| 2009/0112229 A1 | * | 4/2009 | Omori .................... A61B 34/70 606/130 |
| 2009/0138006 A1 | * | 5/2009 | Bales .................. A61B 18/1206 606/33 |
| 2010/0016853 A1 | * | 1/2010 | Burbank ................ A61B 34/30 606/48 |
| 2010/0076474 A1 | * | 3/2010 | Yates ..................... G16Z 99/00 606/170 |
| 2011/0060346 A1 | | 3/2011 | Jensen et al. |
| 2011/0118754 A1 | | 5/2011 | Dachs, II et al. |
| 2011/0208090 A1 | | 8/2011 | Parihar |
| 2013/0214029 A1 | | 8/2013 | Scirica |
| 2014/0001234 A1 | | 1/2014 | Shelton, IV et al. |
| 2016/0100838 A1 | | 4/2016 | Beaupré et al. |
| 2016/0174984 A1 | | 6/2016 | Smith et al. |
| 2016/0220369 A1 | | 8/2016 | Chalekian et al. |
| 2018/0073615 A1 | | 3/2018 | Wixey |
| 2018/0274601 A1 | | 9/2018 | Saito et al. |
| 2019/0201148 A1 | | 7/2019 | Wixey et al. |
| 2020/0253671 A1 | | 8/2020 | Bailey et al. |

OTHER PUBLICATIONS

International Search Report and Written Opinion for Application No. PCT/US2017/050731, dated Dec. 15, 2017, 14 pages.
Vertut, Jean and Phillipe Coiffet, Robot Technology: Teleoperation and Robotics Evoitkon and Development. English translation, Prentice-Hall, Inc., Inglewood Cliffs, NJ, USA 1986, vol. 3A, 332 pages.
U.S. Appl. No. 15/699,441, filed Sep. 8, 2017, Split Nut Drive.
U.S. Pat. No. 10,591,032.
U.S. Appl. No. 16/333,926, filed Mar. 15, 2019, Medical Device Drive System.

* cited by examiner

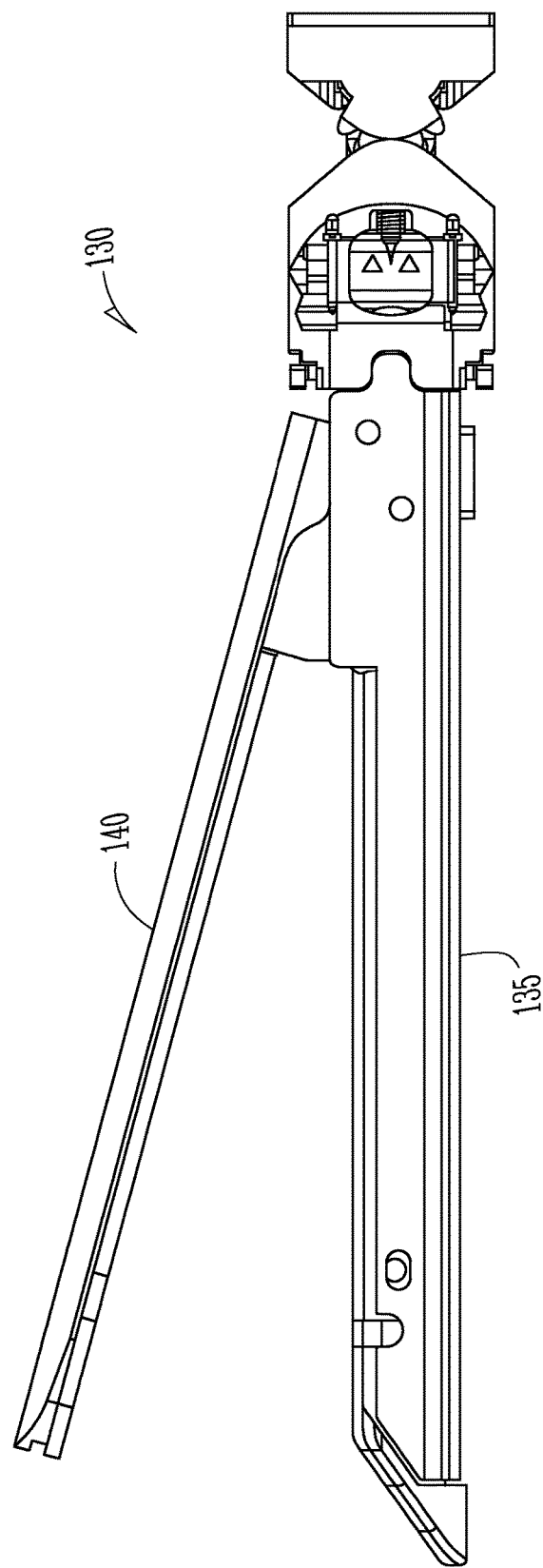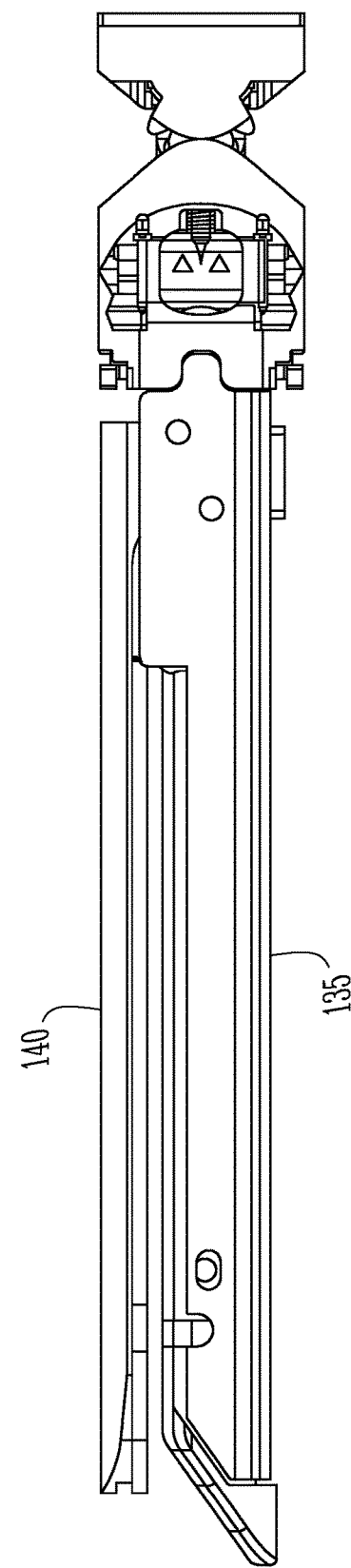

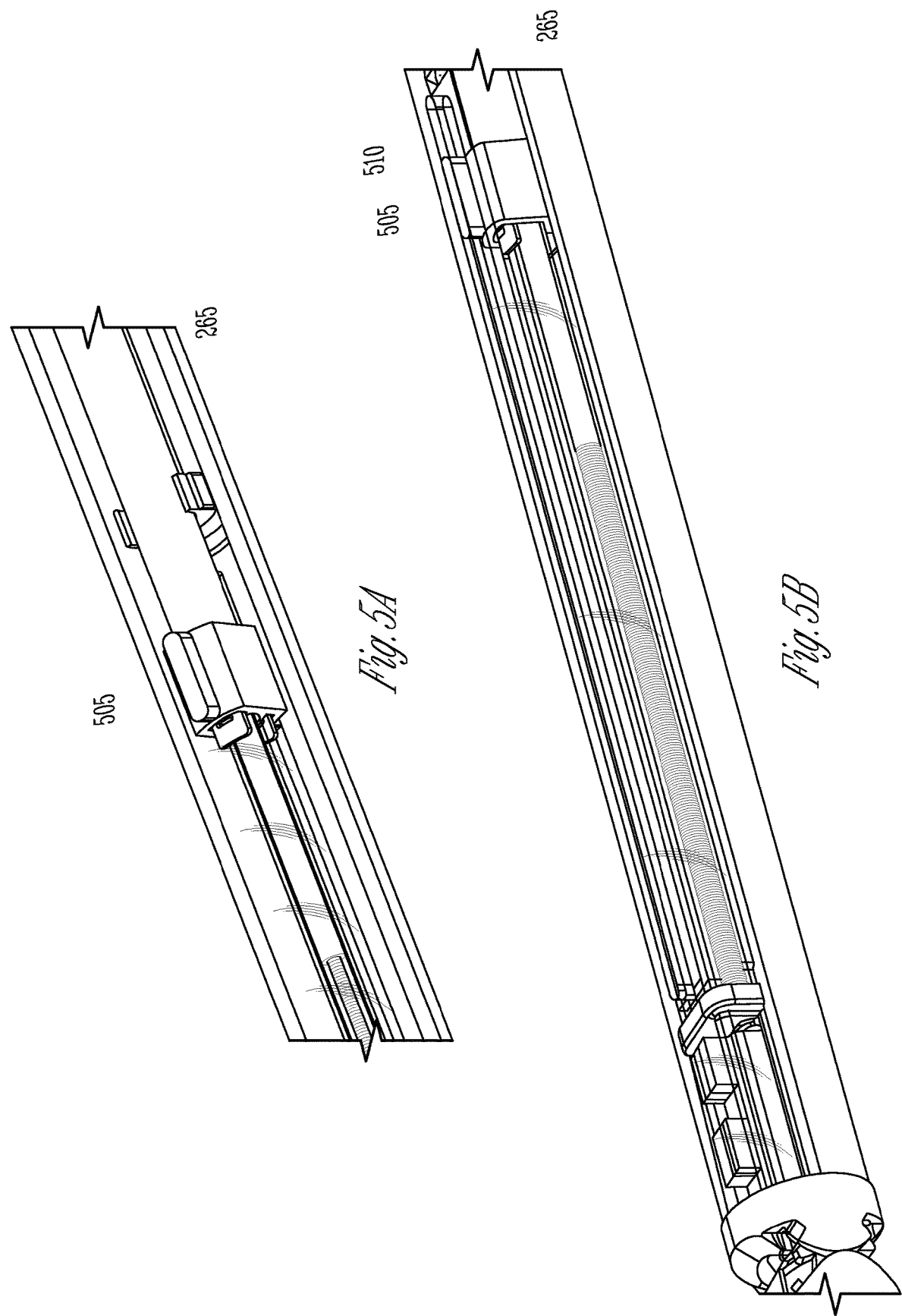

605 — DRIVE BACK-DRIVABLE THREADS ON A FIRST DRIVE MEMBER OF THE FIRST DRIVE SYSTEM IN A FIRST DIRECTION TO ADVANCE THE FIRST DRIVE MEMBER AND A SECOND DRIVE MEMBER OF THE SECOND DRIVE SYSTEM

610 — DRIVE BACK-DRIVABLE THREADS ON THE FIRST DRIVE MEMBER OF THE FIRST DRIVE SYSTEM IN A SECOND DIRECTION TO RETRACT THE FIRST DRIVE MEMBER AND THE SECOND DRIVE MEMBER

615 — DRIVE THREADS ON THE SECOND DRIVE MEMBER TO ADVANCE THE SECOND DRIVE MEMBER, WITHOUT ADVANCING THE FIRST DRIVE MEMBER

620 — DECOUPLE THE SECOND DRIVE SYSTEM FROM THE FIRST DRIVE SYSTEM AND MANUALLY RETRACTING A LEAD SCREW AND SURGICAL INSTRUMENT

*Fig. 6*

MEDICAL DEVICE DRIVE SYSTEM

RELATED APPLICATION

This application is a U.S. National Stage Filing under 35 U.S.C. 371 from International Application No. PCT/US2017/050710, filed on Sep. 8, 2017, and published as WO 2018/052806 A1 on Mar. 22, 2018, which claims the benefit of priority of U.S. Provisional Application 62/395,360, filed Sep. 15, 2016, each of which is herein incorporated by reference in its entirety.

BACKGROUND

Medical device systems can include components that are driven by drive mechanisms such as electric motors. Drive components such as gears, levers, and tubes can be used to translate movement through a drive system to a medical tool. For example, surgical systems can include tools that are controlled and driven by mechanical drive systems. Surgical systems can include tools such as cutters, staplers, and cautery tools.

SUMMARY

An example medical device drive system includes a support structure, a first drive input, and a first drive member slidably coupled to the support structure. The first drive member can be operatively coupled with the first drive input, and can be slidable in a forward direction and a backward direction relative to the support structure. The first drive member being can be drivable by the first drive input in the forward direction and in the backward direction. The example medical device drive system can further include a second drive input, and an intermediate drive member movably coupled to first drive member and operatively coupled with the second drive input. The intermediate drive member can be drivable by the second drive input. The example medical device drive system can further include a second drive member operatively coupled to the intermediate drive member. The second drive member can be drivable by the intermediate drive member in a forward direction. A medical tool can be coupled to the second drive member. Driving the second drive member in a forward direction can effectuates a change in a position or configuration of the medical tool. The first operation can, for example, be movement of a surgical instrument, opening or closing of a tool, or delivery of staples.

In some examples, the second drive member is not back-drivable by the intermediate drive member. In other examples, the second drive member is back-drivable by the intermediate drive member.

In an example, the first drive member can include a back-drivable threaded interface, and the first drive input can include a first drive input threaded interface that is engaged with the back-drivable threaded interface. The second drive member can include a second drivable threaded interface (e.g. a nut) and the intermediate drive member can include a second drivable threaded interface (e.g. threads on a lead screw, which are optionally not back-drivable).

In an example, the first drive member and the first drive input are configured to convert rotational motion of the first drive input into translational movement of the first drive member, and the intermediate member and second drive member are configured to convert rotational movement of the intermediate drive member into translational movement of the second drive member. In an example, the intermediate drive member is a lead screw, the lead screw being rotatably coupled to the first drive member; and the second drive input is configured to turn the lead screw. The lead screw can include a threaded portion, and the second drive member can include a nut having threads engaged with the threaded portion of the lead screw, the threads on the nut being forward-drivable and not back-drivable. In an example, the threaded portion of the lead screw defines a lead screw axis, and the nut is slidably coupled to the support structure. The nut can be slidable along the lead screw axis, and the system can further include a nut restraining feature sized and shaped to restrict rotational movement of the nut, wherein turning the lead screw drives the nut along the lead screw axis.

In some examples, the second drive input can include a drive gear that is coupled to the lead screw, and the system can further include a drive input gear that is operatively coupled with the drive gear.

In some examples, the medical tool can be a surgical tool, and the drive input gear can be coupled to a surgical control system.

In an example, the intermediate drive member can have portions defining a longitudinal axis, and the intermediate drive member is rotatable about the longitudinal axis with respect to the first drive member. The intermediate drive member can be releasably coupled to first drive member. The medical device drive system can have a first state and a second state. In the first state the intermediate drive member is coupled to the first drive member, and the intermediate drive member is not displaceable along the longitudinal axis. In the second state the intermediate drive member is not coupled to the first drive member, and the intermediate drive member, second drive member and the medical tool are displaceable together along the longitudinal axis.

The intermediate drive member can include a circumferential slot, and the medical device drive system can further include a coupling member that is engaged with the circumferential slot. The coupling member can rotatably couple the lead screw to the first drive member.

The first drive member can include portions defining a first orifice extending through the first drive member and adjoining the circumferential slot in the intermediate drive member, the coupling member extending through the first orifice and into the circumferential slot.

In some examples, driving the first drive member in a forward direction effectuates a first operation of the medical tool at a first rate, and driving the second drive member forward effectuates the first operation of the medical tool at a second rate, the second rate being smaller than the first rate. In an example, an interface between the first drive input and the first drive member defines a first drive ratio, and an interface between the second drive input and the intermediate drive member defines a second drive ratio, the first drive ratio being larger than the second drive ratio.

In some examples, driving the first drive member in a forward direction effectuates a first operation of the medical tool, and driving the second drive member in a forward direction effectuates a second operation of the medical tool. In an example where the medical tool is a surgical stapler, the first operation of the tool can be closing jaws of a surgical stapler, and the second operation can be advancing the cartridge of a surgical stapler.

A medical device system with a coarse adjustment system and a fine adjustment system in series can include a support structure, a first drive gear rotatably coupled to the support structure, the first drive gear having a first drive gear interface and a drive gear threaded interface, a coarse adjustment drive member slidably coupled to the support structure, the coarse adjustment drive member having a coarse adjustment threaded interface that is engaged with the drive gear threaded interface, the coarse adjustment drive member being forward-drivable and backward-drivable by the first drive gear, a lead screw rotatably coupled to the coarse adjustment drive member, the lead screw having a lead screw threaded interface; and a second drive gear coupled to the lead screw, the second drive gear having a second drive gear interface. The medical device system can further include a fine adjustment drive member slidably coupled to the support structure, the fine adjustment drive member having a fine adjustment threaded interface engaged with the lead screw threaded interface, the fine adjustment drive member being forward-drivable by the lead screw, and the fine adjustment drive member not being backward-drivable by the lead screw. The medical device system can further include a surgical tool coupled to the lead screw.

In an example, the first drive gear interface can include internal threads, and the coarse adjustment threaded interface can include external threads that are engaged with the internal threads of the first drive gear interface.

In an example, the coarse adjustment drive member can include an internal chamber and the lead screw extends through the internal chamber.

In an example, the medical device system can further include a surgical tool coupled to the fine adjustment drive member. The surgical tool can be coarsely adjustable by movement of the first drive gear and the surgical tool being finely adjustable by movement of the second drive gear.

In an example, the medical device system can further include a surgical control system. The surgical control system can include a first control gear engaged with the first drive gear and a second control gear engaged with the second drive gear.

In an example, the medical device can further include a coupling member sized and shaped to selectively couple and decouple the lead screw to the first drive member.

An example medical device system can include a housing having portions defining a housing chamber, the housing chamber having a proximal end and a distal end defining an axis extending between the proximal end and the distal end, a first drive member in the housing chamber, the first drive member being slidable in the housing chamber along the axis, the first drive member having a back-drivable threaded interface, and a first drive member internal chamber extending through the first drive member. The medical device system can further include a first drive gear rotatably coupled to the housing, the first drive gear having a second threaded interface engaged with the back-drivable threaded interface of the first drive member, wherein turning the first drive gear drives the first drive member along the axis in the housing. The medical device system can further include a lead screw rotatably coupled to the first drive member, the lead screw having a proximal end and a distal end, a body portion from the proximal end to the distal end, the body portion extending through the first drive member internal chamber, and the lead screw further including lead screw threads proximate the distal end. The medical device drive system can further include a second drive gear coupled to the proximal end of the lead screw, wherein turning the second drive gear rotates the lead screw with respect to the first drive member, and a second drive member coupled to the distal end of the lead screw, the second drive member having second drive member threads engaged with the lead screw threads, the second drive member threads not being back-drivable. The medical device drive system can further include a surgical tool coupled to the second drive member. In an example, turning the first drive gear in a first direction advances the first drive member, lead screw, and second drive member, and turning the first drive gear in a second direction retracts the first drive member, lead screw, and second drive member, turning the second drive gear advances the second drive member.

In an example, turning the second drive gear advances the second drive member, but does not advance the first drive member.

In an example, turning the first drive gear in a first direction effectuates a first operation of the surgical tool, turning the first drive gear in the second direction reverses the first operation of the surgical tool, and turning the second drive gear effectuates a second operation of the surgical tool. In an example where the surgical tool is a stapler, turning the first drive gear opens the jaws of the stapler, turning the first gear in the second direction closes the jaws of a stapler, and turning the second drive gear delivers staples.

In an example, the medical device drive system includes a coupling member sized and shaped to selectively couple and decouple the lead screw to the first drive member.

In an example, the medical device drive system has a first state and a second state. In the first state the coupling member is engaged with the first drive member and the lead screw and the lead screw is axially fixed relative to the first drive member by the coupling member. In the second state, the coupling member is disengaged from the lead screw and the lead screw is axially displaceable relative to the first drive member.

In an example, the medical device drive system has a disengaged state and an engaged state. In the disengaged state the first drive member is in a first position in the housing chamber, and the surgical tool is in a disengaged configuration. In the engaged state the first drive member is in a second position in the housing chamber, and the surgical tool is in an engaged configuration. In an example, the medical device drive system further includes a bias member in the housing chamber, the bias member being sized and shaped to bias the first drive member toward the first position in the housing chamber, wherein the bias member biases the surgical tool to the disengaged configuration. In an example the bias member is a spring.

An example method of adjusting the position or configuration of a surgical instrument using a first drive system and a second drive system that are arranged in series and coupled to each other and to the surgical instrument can include driving back-drivable threads on a first drive member of the first drive system in a first direction to advance the first drive member and a second drive member of the second drive system, driving back-drivable threads on the first drive member of the first drive system in a second direction to retract the first drive member and the second drive member, and driving non back-drivable threads on the second drive member to advance the second drive member, without advancing the first drive member. Advancing the first drive member effectuates a first change in position or configuration of the surgical instrument, and advancing the second drive member effectuates a second change in the position or configuration of the surgical instrument.

In an example, advancing the driving the back-drivable threads on the first drive member effectuates a first operation of the surgical instrument, and driving the non-back-drivable threads on the second drive member effectuates a second operation of the surgical instrument.

In an example, driving the back-drivable threads on the first drive member advances the second drive member and the surgical tool at a first forward advancement rate, and driving the non-back-drivable threads on the second drive member advances the second drive member and surgical tool at a second forward advancement rate, the second forward advancement rate being smaller than the first forward advancement rate.

In an example, driving the back-drivable threads on the first drive member includes rotating a gear that has internal threads that interface with external threads on the first drive member.

In an example, driving the non-back-drivable threads on the second drive member includes rotating a lead screw that has external threads that engage internal threads on the second drive member, the second drive member being prevented from rotation, wherein rotating the lead screw causes linear displacement of the second drive member relative to the lead screw. In an example, the method further includes decoupling the second drive system from the first drive system and manually retracting the lead screw and surgical instrument.

An example medical device drive system includes a support structure, a first drive member coupled to the support structure, the first drive member including an internal chamber, an elongated member extending through the internal chamber in the first drive member, the elongated member having a proximal end, a distal end, and an elongated body extending from the proximal end to the distal end, the elongated body defining an axis, the elongated member being rotatable in the internal chamber about the axis and retractable along the axis through the first drive member, and a coupling member releasably coupling the elongated member to the first drive member, the coupling member preventing translational movement of the elongated member relative to the first drive member, and not preventing rotational movement of the elongated member relative to the first drive member, wherein when the coupling member is decoupled from the elongated member, the elongated member is retractable through the internal chamber of the first drive member.

In an example, the elongated member can include a circumferential slot and the first drive member can include portions defining a first orifice through the first drive member and adjoining the circumferential slot, the coupling member extending through the first orifice into the circumferential slot. In an example, the first drive member can include portions defining a second orifice extending through the first drive member and adjoining the circumferential slot, and the coupling member can include first segment extending through the first orifice into the circumferential slot and a second segment extending through the second orifice and into the circumferential slot.

Each of these non-limiting examples can stand on its own, or can be combined in various permutations or combinations with one or more of the other examples.

This Summary is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 4A is an illustration of a medical device tool in an open configuration.

FIG. 4B is an illustration of a medical device tool in a close configuration.

FIG. 5A is an illustration of an example drive member and an anti-rotation block.

FIG. 5B shows the anti-rotation block engaged in a slot in the drive system.

FIG. 6 is a flowchart illustration of an example method.

DETAILED DESCRIPTION

Medical device drive systems can be used to control an instrument that is coupled to a drive system with a shaft. A teleoperated surgical system, for example, can employ a medical device drive system to control a surgical instrument that can be inserted into a patient to perform a surgical procedure.

Manipulation of a surgical instrument during a teleoperated surgical procedure can be difficult, due to factors such as space constraints, the size of components, the need for precision and accuracy during surgery, and the presence of multiple tools in the body.

An example medical device drive system can include two (or more) drive sub-systems that operate in series. For example, a first drive sub-system that is controllable through a first drive input can be configured to move a second drive sub-system that is controllable through a second drive input. The second drive sub-system can be coupled to a medical tool, such as a surgical instrument. Because the second drive sub-system and surgical tool are movable by the first drive sub-system, different types of tool manipulations can be accomplished through the first drive input and second drive input.

An example system can include an intermediate drive member that joins the first drive sub-system with the second drive sub-system. The intermediate drive member can include two drive interfaces: one that interfaces with the first drive sub-system, and a second drive interface that interfaces with the second drive sub-system. In an example, the intermediate drive member includes back-driveable threads that interface with the first drive sub-system, and a gear interface that interfaces with the second drive sub-system.

Other combinations are possible. For example, the first drive sub-system or the second drive sub-system could be a rack and pinion system, a helical gear, back-driveable threads, or a gear. In various configurations, the intermediate member can include an interior chamber or bore that includes an interface, such that one of the first drive sub-system and second drive sub-system can interface with an interface feature in the interior chamber or bore, and the other sub-system can interface with an exterior interface feature.

In an example configuration, a system can be configured so that the first drive system moves the tool faster than the second drive system: The first drive system can, for example, be configured as for coarse adjustment, and the second drive system can be configured as for fine adjustment. In another example, the first drive system can be configured to move or position a tool, and the second drive system can be configured to control an operation of a tool, such as delivery of staples. In another example, the first drive system can control a first operation of a tool, such as closing or opening jaws of a stapler, and the second drive system can control a second operation of the tool, such as delivery of staples.

Figure 1A:
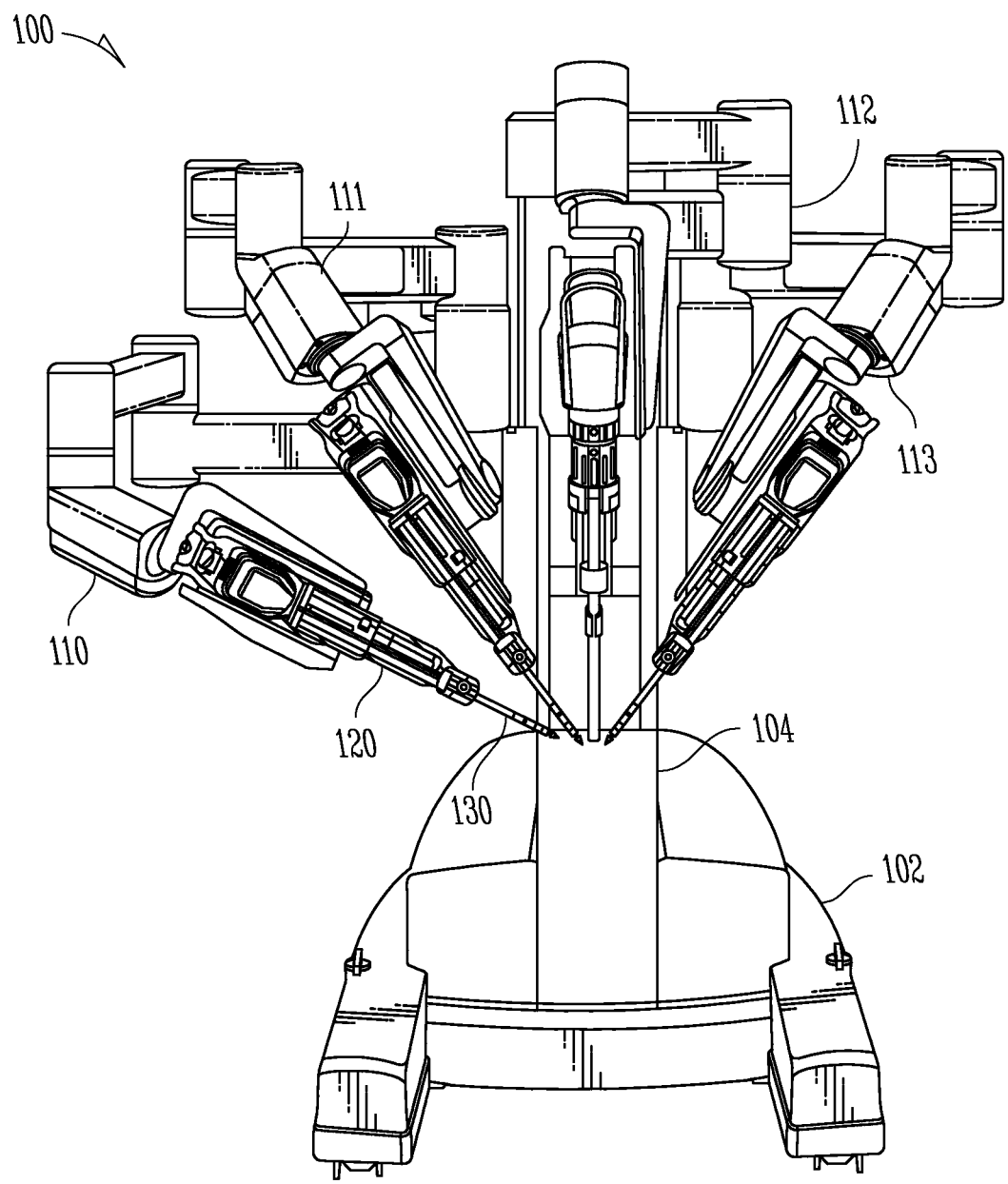
FIG. 1A is an illustration of an example instrument system for use in robot-assisted minimally invasive surgery.
Figure 1B:
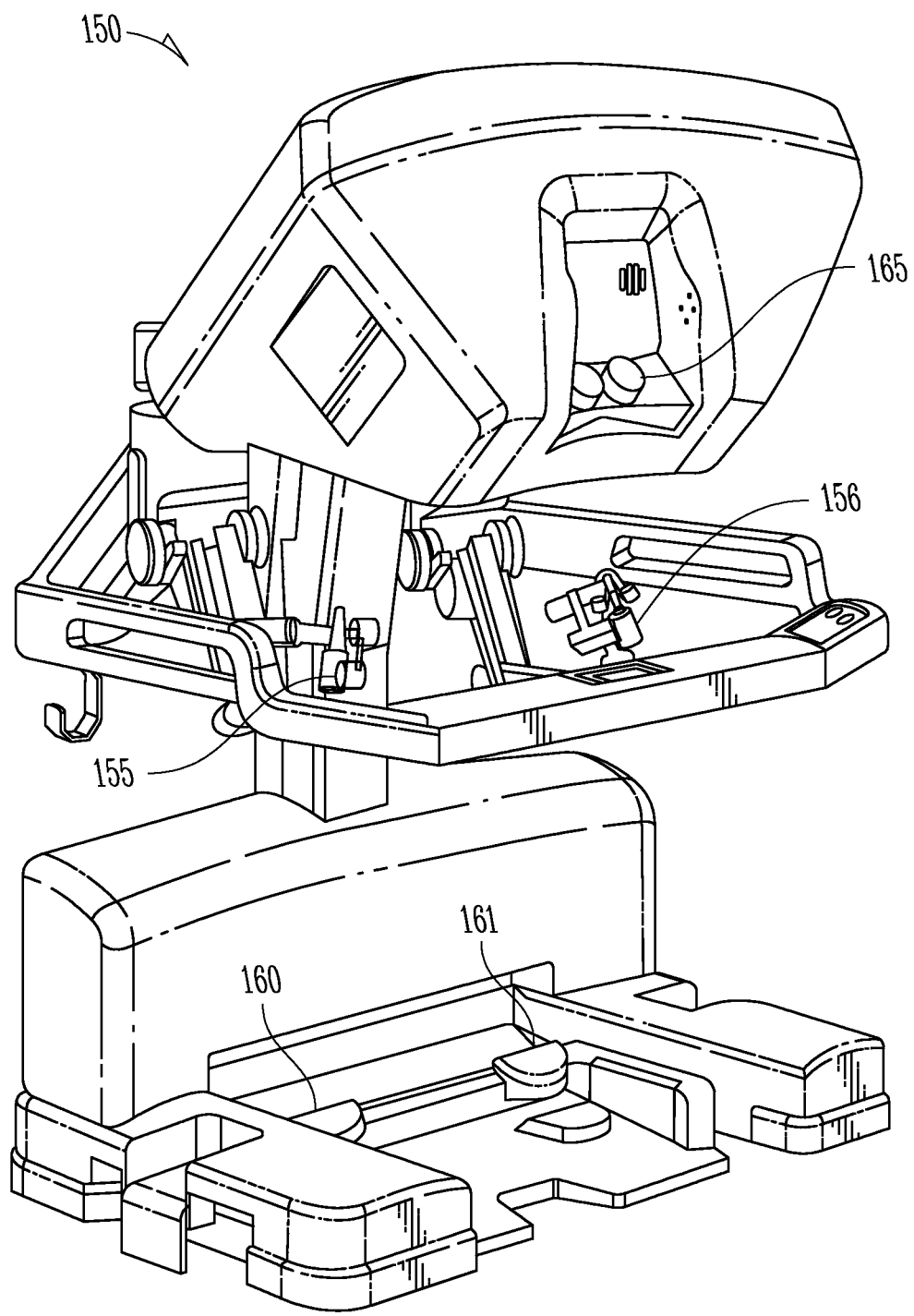
FIG. 1B is an illustration of an example physician console for use in robot-assisted minimally invasive surgery.
Figure 1C:
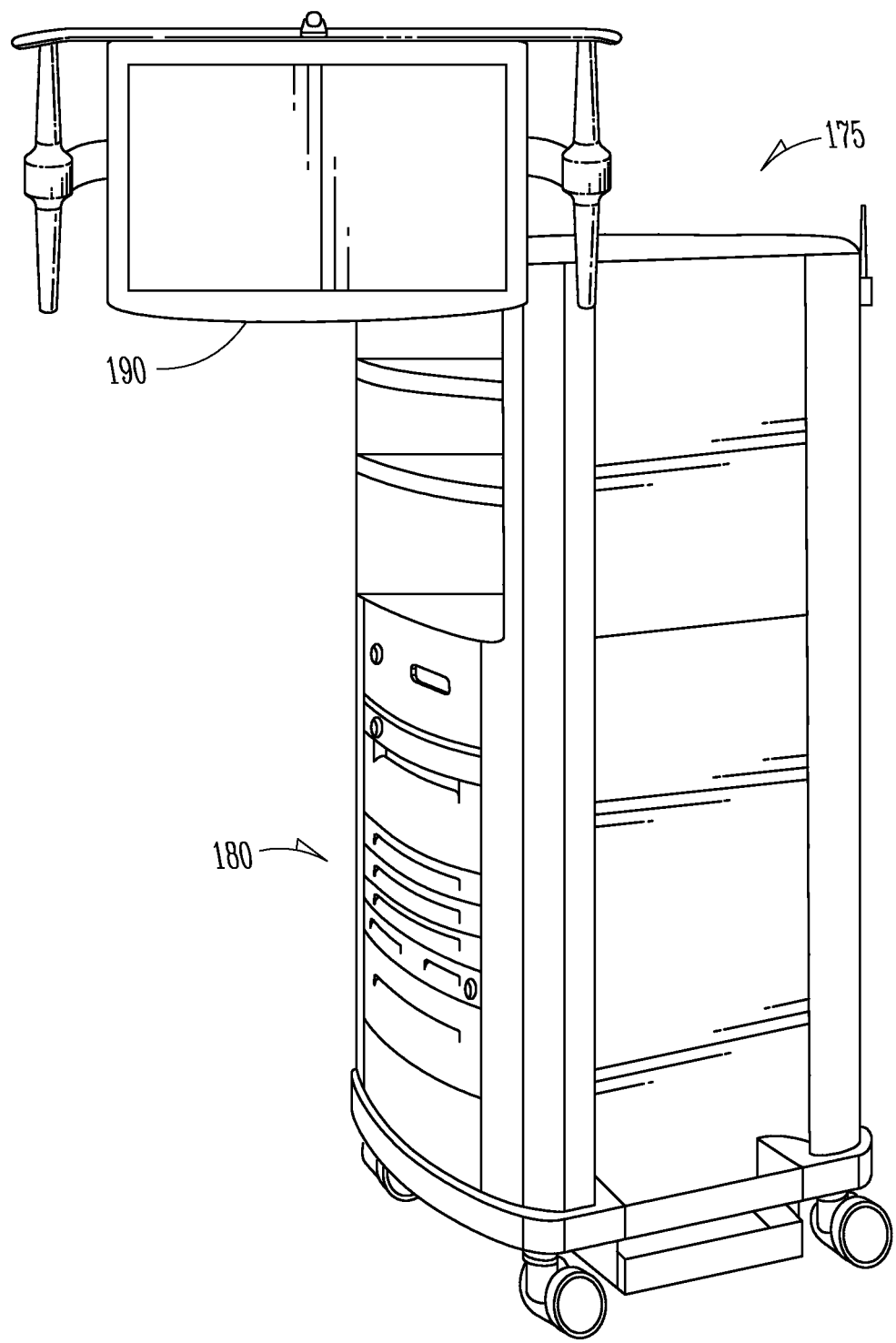
FIG. 1C is an illustration of an example control cart for use in robot-assisted minimally invasive surgery.

FIGS. 1A, 1B, and 1C illustrate an example robot-assisted minimally invasive surgical system. FIG. 1A shows an instrument system 100 (sometimes known as a "patient side cart") that can be situated near a patient operating table (not shown). FIG. 1B shows a surgeon console 150 that can include controls and a viewing system. FIG. 1C shows a control cart 175 that can include, for example, processing equipment and communication equipment.

Referring again to FIG. 1A, the system 100 can include a base 102, a support tower 104, and one or more manipulator arms 110, 111, 112, 113, which can be mounted on the support tower. Alternatively, the manipulator arms 110, 111, 112, 113 can be connected to a main boom (not shown), which can be movable. An instrument 130 can be mounted to an instrument mount 120 on one of the manipulator arms. A cannula (not shown in FIG. 1A) can be mounted to a cannula mount. An instrument 130 can be inserted through a cannula seal in the cannula, and into the patient (not shown) for use in a surgical or other medical procedure. Through movement of the manipulator arms, the orientation of the instrument can be controlled in multiple dimensions, e.g. lateral, horizontal, vertical, angular movements in one, two, or three planes.

FIG. 1B shows an example physician console 150. The physician console can include hand control 155, 156 and pedal controls 160, 161. The hand controls 155, 156, and pedal controls 160, 161 can be used to control equipment at the patient side cart. For example, portions of a distal end of an instrument can be manipulated using instrument controls. The controls can include haptic feedback features so that a physician can interpret physical information, such as resistance or vibration, through the controls. The physician console 150 can also include a viewing system 165 that can display video or other images of a surgical site.

FIG. 1C shows an example control cart 175. The control cart can include processing equipment 180 for processing controls, facilitating communication between the physician console and the patient side cart, or a remote site. The control cart 175 can also include a display 190, which can show images that the physician is seeing on the physician console, a video feed from a camera in the patient, or other information. In an example configuration, signals input at a surgeon console 150 can be transmitted to the equipment 180 on the control cart, which can interpret the inputs and generate commands that are transmitted to the patient side cart 100 to cause manipulation of an instrument 130 or portions of a manipulator arm 110. The equipment 180 is shown on a cart for exemplary purposes, but could also be arranged in various configurations, e.g., it could be integrated as part of the physician console, the patient side cart, or both, or divided between the physician console and patient side cart. The equipment can also be provided as software, hardware, or both, on an installed or remote system.

Figure 1D:
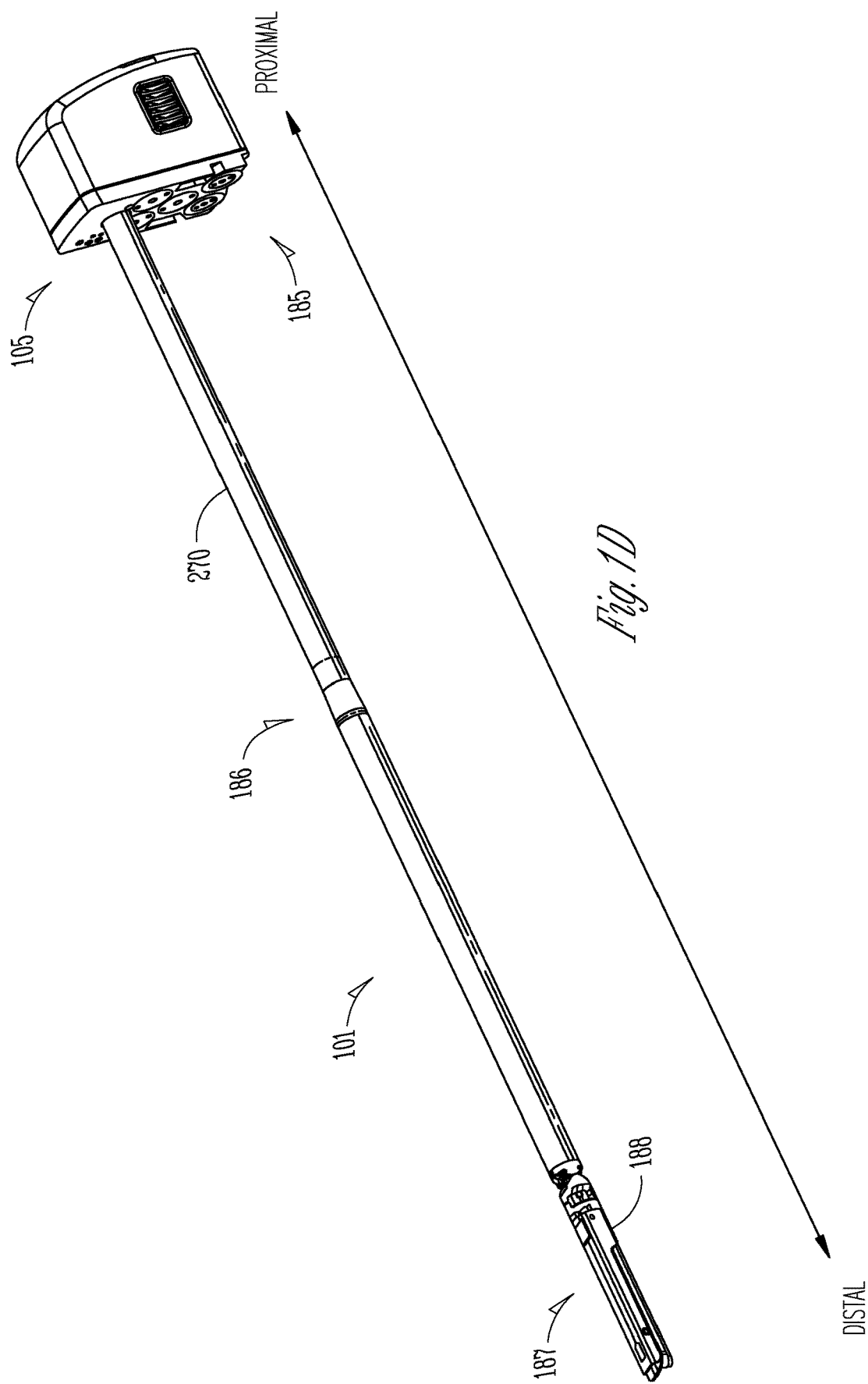
FIG. 1D is a perspective view of an example medical device drive system connected to an example medical tool.

FIG. 1D shows an example medical device system 101 that can be mounted on and used with the instrument system 100 shown in FIG. 1A. The medical device system 101 can include a proximal portion 105 including an interface 185 that can couple to a computerized control system such as the system illustrated in FIGS. 1A, 1B, and 1C, a middle portion 186 that can include drive components such as a drive member (not shown in FIG. 1D), and a distal portion 187 that can include an surgical tool 188. The surgical tool 188 can, for example, be any of a variety of surgical tools, such as a cutter, grasper, a cautery tool, a camera, a light, or a surgical stapler. The surgical tool 188 can be the instrument 130 shown in FIG. 1A. For the purpose of this document, the terms "tool" and "instrument" are interchangeable.

Figure 2A:
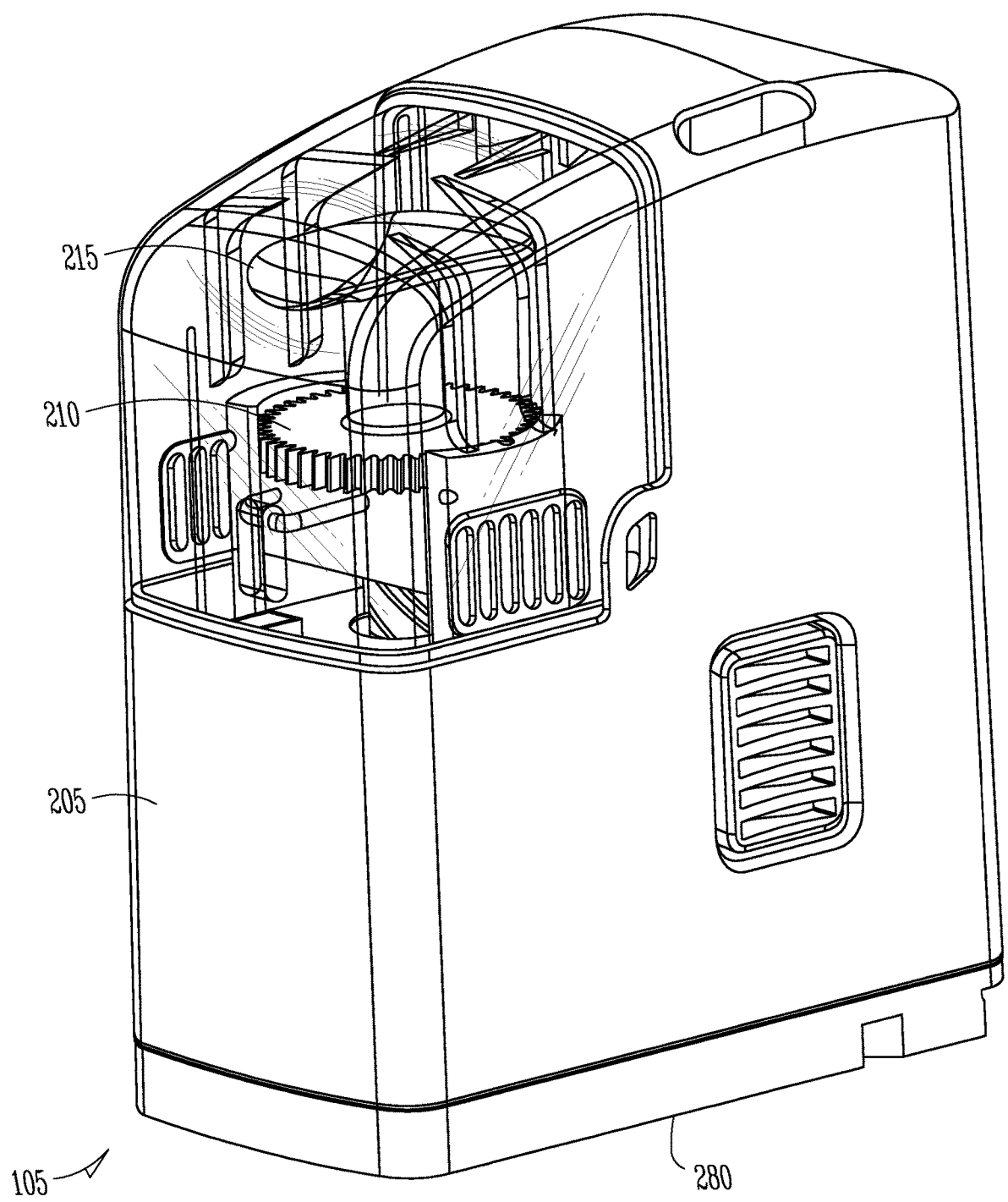
FIG. 2A is a perspective view of a proximal end of the medical drive system of FIG. 1D.

FIG. 2A shows the proximal portion 105 of the medical device system 101. The medical device system 101 can include a main housing 205 and a removable cover 210 coupled to the main housing 205. The main housing can be coupled to a mounting plate 280.

The medical device system 101 can include drive sub-systems that are configured in series and coupled to drive components and a medical tool, such as a surgical tool.

Figure 2B:
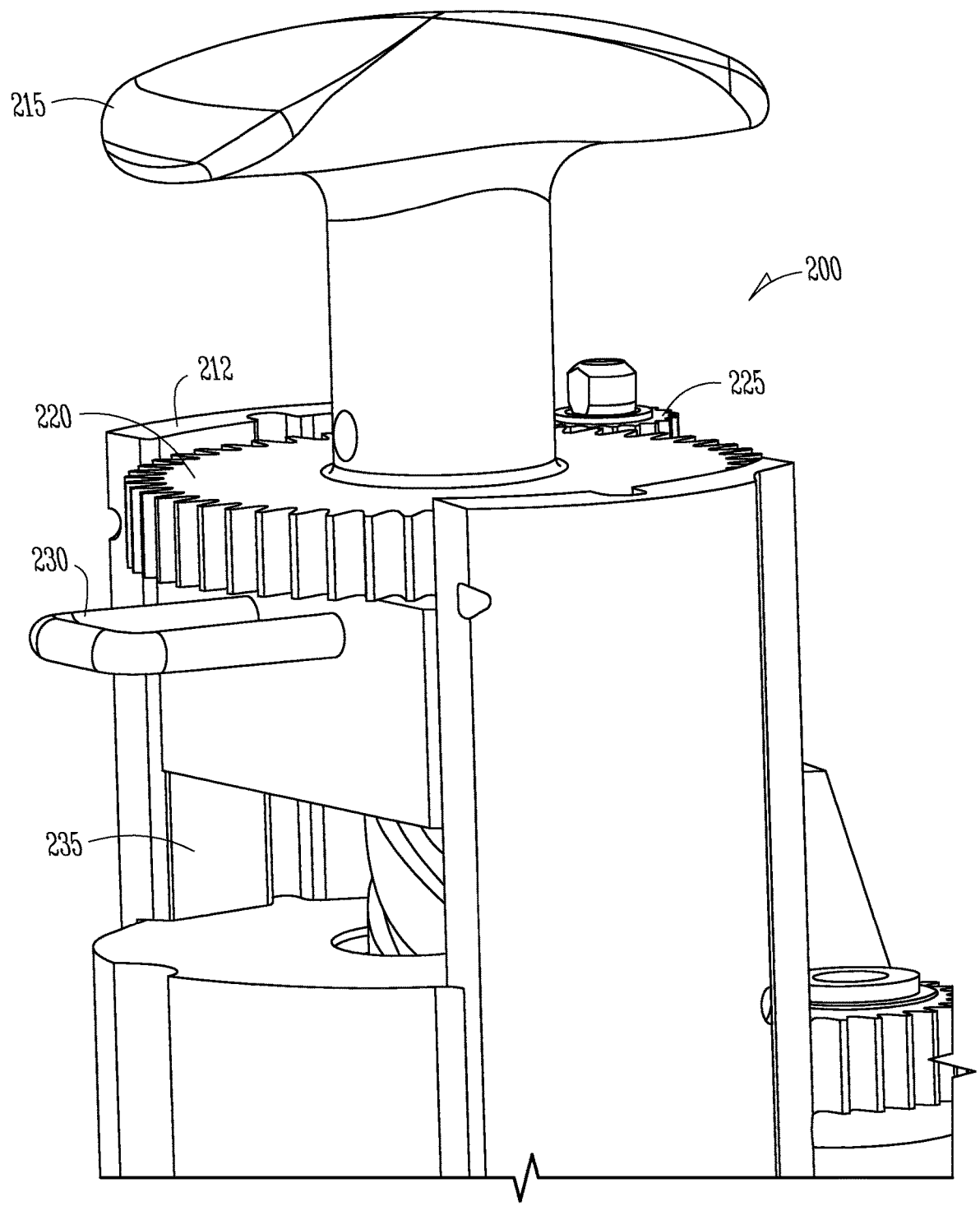
FIG. 2B is a perspective view of a drive gear, drive member, pull pin and other internal components of the proximal end of a medical device drive system.
Figure 2C:
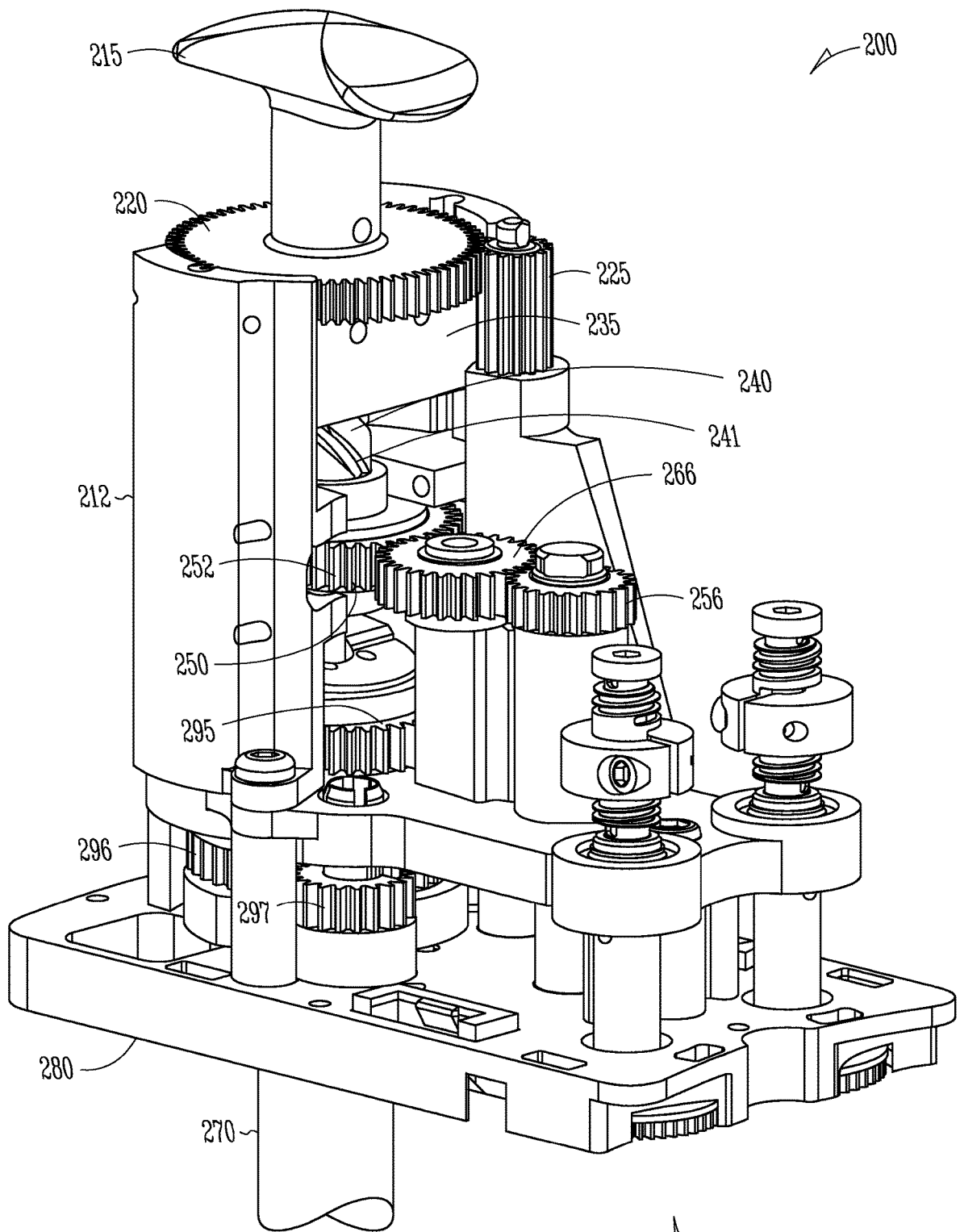
FIG. 2C is a perspective view of drive components in a medical device drive system.
Figure 2D:
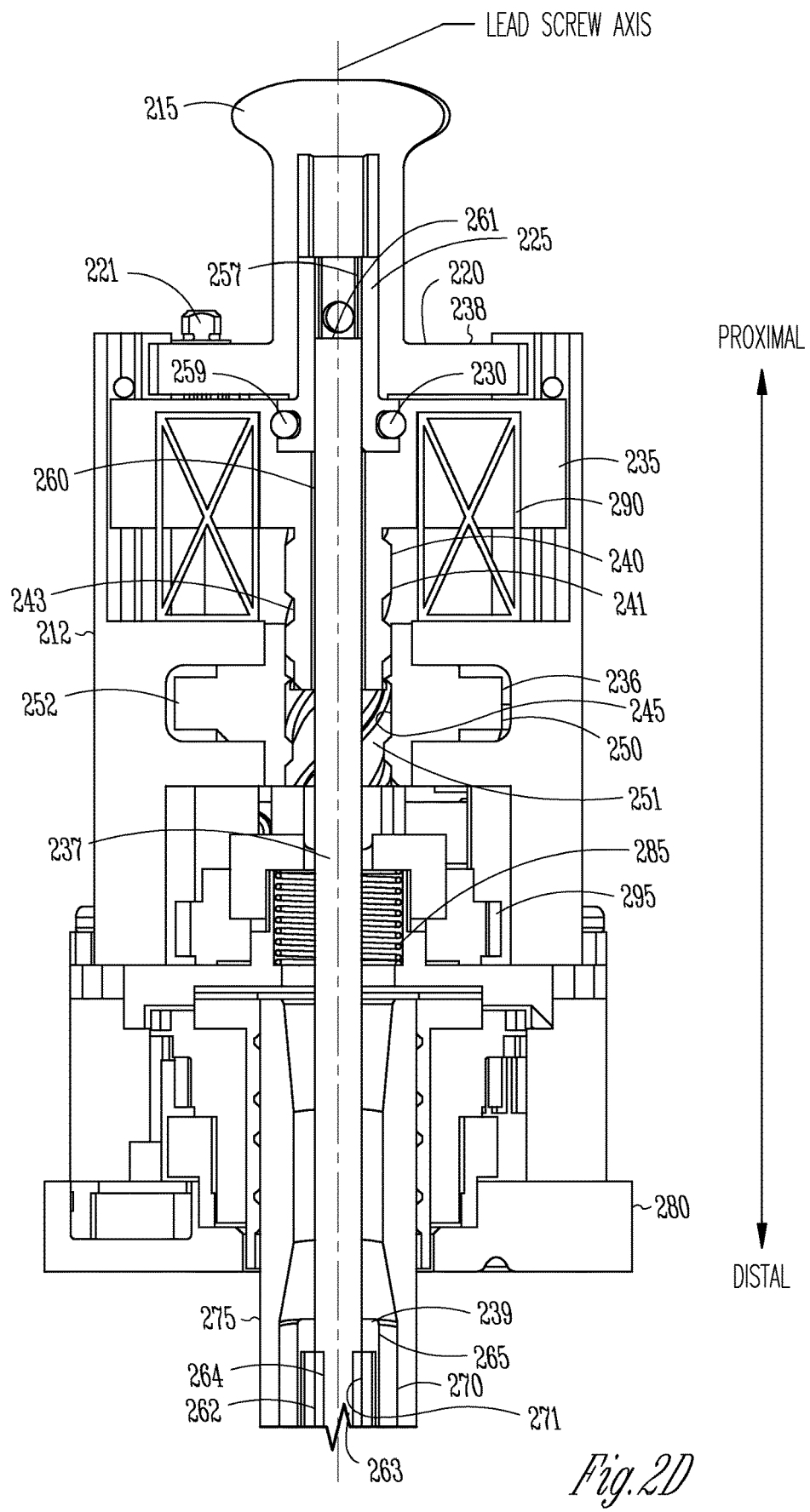
FIG. 2D is a cross-sectional view of drive components in a medical device drive system.

FIG. 2B is a perspective view of some of the drive components in a proximal portion 200 of the drive system aspects of the medical device system 101. FIG. 2C is a more complete illustration of the proximal portion 200 of the drive system shown in FIG. 2B. FIG. 2D is a cross-sectional view of the proximal portion 200 of the medical device drive system.

As shown in FIGS. 2B, 2C, and 2D, the proximal portion 200 of the drive system can include a first drive member 235 that is situated in a support structure 212 that can include or be coupled to the mounting plate 280. The first drive member 235 can be slidably disposed in a chamber in the support structure 212. In an example, the first drive member can be slidable in a forward direction toward a distal end of the medical device system 101 (i.e., down in FIGS. 2C and 2D), and slidable in a backward direction toward a proximal end of the medical device drive system. A bias member 290 such as a spring can be provided in the support structure 212 and configured to bias the bias member 290 toward a proximal position.

The first drive member 235 can be operatively coupled to a first drive input 236, which can be configured to drive the first drive member in the forward direction and in the backward direction. In an example, the first drive member 235 and first drive input 236 can be configured to convert rotational movement of the first drive input 236 into translational movement of the first drive member 235. This can be accomplished, for example, using a back-drivable threaded interface between the first drive input 236 and the first drive member 235. An intermediate drive member 237 can be movably coupled to the first drive member 235. For example, the intermediate drive member 237 can be rotatably coupled to the first drive member 235. In other examples, the intermediate drive member 237 can slidable relative to the first drive member (e.g., slidable down a bore or through an opening in the first drive member), or both rotatable and slidable relative to the first drive member (e.g. actuatable on internal threads on a bore on the first drive member.) A second drive input 238 can be operatively coupled to the intermediate drive member 237 and configured to drive the intermediate drive member. In some examples, a second drive member 239 can be operatively coupled to the intermediate drive member 237. For example, the second drive member 239 can be driveable in the forward direction by the intermediate drive member 237 using, for example, a threaded interface. In an example, the second drive member 239 can include a drivable threaded interface (e.g., a nut) and the intermediate drive member 237 can include drivable threads on a lead screw, which are optionally back-drivable, or not back-drivable. A medical tool can be coupled to the second drive member.

Referring again to FIGS. 2C and 2D, the first drive member 235 can be coupled to a threaded member 240 that extends distally from the drive member. In an example, the threaded member 240 can be connected to the drive member. In another example, the threaded member 240 can be formed as part of the first drive member 235. The threaded member 240 can include an interface portion 241. The interface portion 241 can, for example, include a back-drivable threaded interface 242 that includes back-drivable threads 243.

A first drive gear 250 can include a threaded interface portion 245 that is configured to operatively couple with the interface portion 241 on the threaded member 240. In an example, the first drive gear 250 can include internal threads 251 that interface with external back-drivable threads 243 on the threaded member 240. The first drive gear 250 can include a second drivable interface, which can for example be a gear interface 252. The gear interface 252 can be configured to interface with a first drive input gear 256, which can be operatively coupled with a telerobotic surgical system to enable control through a user interface. In an example, the first drive input gear 256 is coupled to reduction gear 257 which is coupled to the first drive gear 250.

A second drive gear 220 can be coupled to the first drive member 235. A handle 215 can optionally be connected to the second drive gear 220. In an example, the second drive gear 220 can be coupled to the first drive member 235 with a coupling member 230, which can, for example, extend through an orifice in the first drive member. The coupling member 230 can, for example, be a pull pin. When the coupling member 230 is engaged, the second drive gear 220 and lead screw 260 can be axially fixed relative to the first drive member 235. When the coupling member 230 is disengaged, (e.g., when pull pin is removed), the second drive gear 220 and lead screw 260 can be axially displaceable relative to the first drive member. For example, the handle 215 can be pulled in the proximal direction by a user, which can proximally displace the second drive gear 220 and lead screw 260 along the lead screw axis.

In an example, the coupling member 230 can engage a connector 255, which can be coupled to the second drive gear 220. The connector 255 can also be an extension of or integral with the second drive gear 220. The connector 255 can be engaged by the coupling member 230 in a manner that allows the second drive gear 220 to rotate with respect to the first drive member 235. In an example, the connector 255 has a circumferential groove 262 that receives the coupling member 230, so that the connecting member is axially restrained (along the lead screw axis) relative to the first drive member 235, but permitted to rotate relative to the first drive member 235.

Referring again to FIG. 2D, an intermediate drive member such as a lead screw can 260 be coupled to the second drive gear 220. In an example, the lead screw 260 can be coupled to the connecting part 255 which is coupled to the second drive gear 220. The connecting part 255 can include an interior chamber 257 that is sized and shaped to receive a proximal end 261 of the lead screw 260. In an example, the lead screw 260 connected to connecting part 255 by a press fit, adhesive, or threads.

Figure 3A:
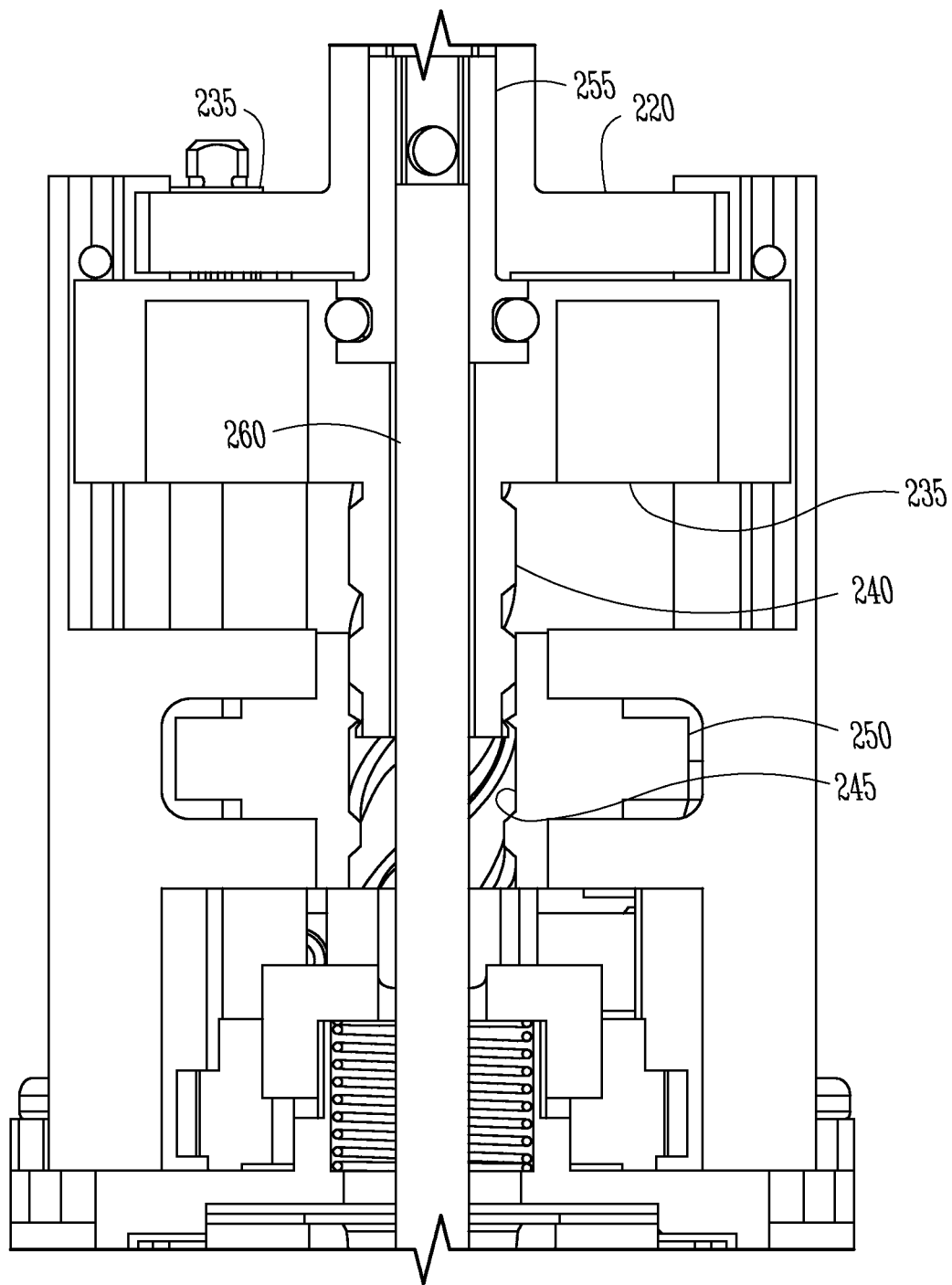
FIG. 3A is a cross-sectional view of portions of a medical device drive system in a first configuration.
Figure 3B:
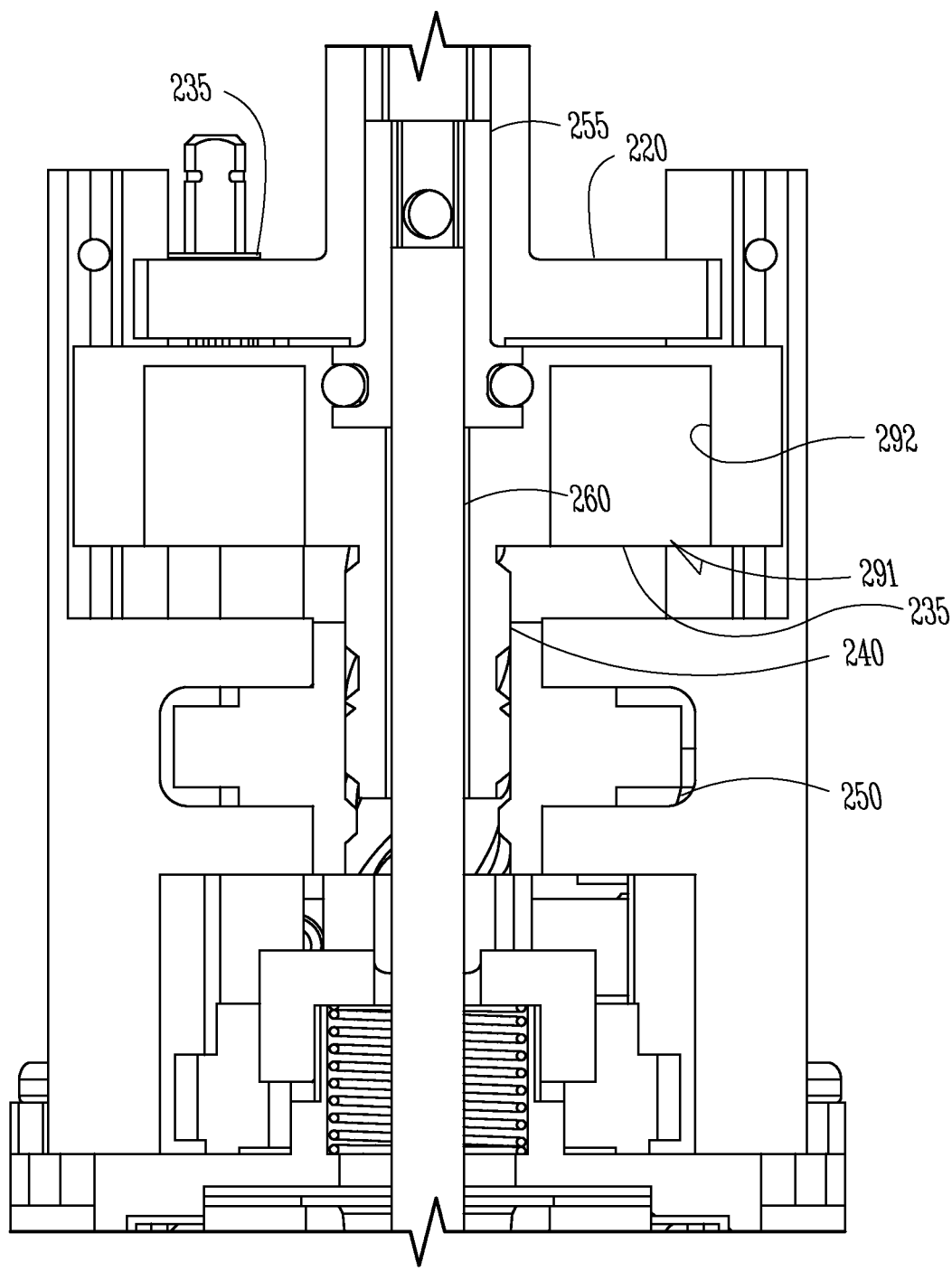
FIG. 3B is a cross-sectional view of portions of a medical device drive system in a second configuration.

In an example, the first drive member 235, second drive gear 220, and lead screw 260 can move together with respect to the support structure 212 from a proximal position (shown in FIGS. 2D and 3A) toward a more distal position (shown in FIG. 3B.)

A second drive input gear 225 can be engaged with the second drive gear 220. The second drive input gear 225 can be controlled using a control system of a telerobotic surgical system, which, for example, can receive operational instructions from a physician using hand controls or other inputs. The telerobotic surgical system can, for example, be the da Vinci® surgical system available from Intuitive Surgical®.

The medical device drive system can also include a second drive member 265. The second drive member 265 can optionally include internal or external threads. The second drive member can, for example, be a nut. In some examples, the nut can be coupled to a drive tube, or the nut can include a drive tube (e.g. a drive tube can include internal threads). The second drive member 265 can alternatively be, or include other structures, such as a rod or a coil.

The lead screw 260 can include an engagement portion 262 that is configured to engage with the second drive member 265. In an example, a distal portion 263 of the lead screw 260 can include a distal threaded interface 264 that can be sized and shaped to engage with an interface portion 271 of the second drive member 265. The threaded interface between the lead screw 260 and the second drive member 265 can optionally be backdriveable, or non-backdriveable. In some examples, the second drive member 265 can be coupled to the lead screw 260 using structures other than threads. For example, a rack and pinion system or helical gear system can be used to couple lead screw 260 to second drive member 265.

In an example, rotation of the first drive gear 250 in a first direction causes the interface portion 245 of the first drive gear 250 to engage with the interface portion 241 on the threaded member 240, which drives the threaded member, first drive member 235, lead screw 260, and second drive member 265 in a distal direction. In the case where the threads are back-drivable, rotation of the first drive gear 250 in a second direction opposite of the first direction can cause the threaded member 240, first drive member 235, and lead screw 260 to move in a proximal direction.

In an example, rotation of the second drive gear 220 drives the second drive member 265 in a distal direction. In an example, the second drive gear can move the second drive member 265, but does not move the first drive member.

In an example, the second drive member 265 can be fixed from rotation, as will be more fully described in reference to FIG. 5. When the second drive member 265 is prevented from rotating, rotation of the lead screw 260 can cause the drive member to move along the lead screw axis. Rotational motion of the lead screw 260 can in this manner be converted to axial motion of the second drive member 265.

Additional gears 295, 296 can also be provided to effectuate other movements of a surgical tool. The other gears can also be coupled to the telerobotic surgical system. For example, gear 297 can engage with gear 296 to turn gear 296 effectuate a change in the status of the surgical tool. Interface portions 121, 122 can be configured to interface with corresponding components (not shown) that are controllable by the telerobotic surgical system.

In an example, removal of the coupling member 230, for example by pulling on the connecting member to withdraw it from the connecting member, can allow proximal movement of the second drive gear 220, first drive member 235, and lead screw 260. For example, a user could pull on handle 215 to manually retract the handle, gear, drive member, other connected components, and a surgical tool.

FIGS. 3A and 3B show the first drive member 235 and second drive gear 220 in a proximal position and a distal position. In an example, second drive input gear 225 can translate with second drive gear 220, as indicated in FIG. 3B. In addition or alternatively, input gear 225 can be long enough that gear 220 can slide distally without disengaging from second drive input gear 225, as shown by the length of second drive input gear 225 in FIG. 2C.

In various examples, the two threaded interfaces between first drive member 235 and first drive gear 250, and between the distal interface of the lead screw and the second drive member 265, can drive different operations of the tool (e.g. opening, closing, cutting, etc.), or a similar movement of the tool in different degrees (e.g. proximal or distal displacement), or a combination of both.

FIGS. 4A and 4B illustrate an example where the drive system includes a surgical stapler 188 having a lower jaw 135 and an upper jaw 140. In an example, in a first state where the first drive member 235 is in a proximal position as shown in FIG. 3A, the stapler jaws 135, 140 are in an open configuration. In a second state where the first drive member 235 is in a distal position as shown in FIG. 3B, the stapler jaws 135, 140 are in a closed position. In an example, actuating the first drive input gear 256 (shown in FIG. 2C) to advance the first drive member 235 closes the jaws 135, 140 of the surgical stapler 188, and actuating the drive input gear 225 to advance the second drive member 265 advances the cartridge of a surgical stapler 188.

In an example, the distal threaded interface 264 and interface portion 271 of the drive member can have threads that are more fine—i.e. have a higher pitch count—than the threads on the interface portion 241 on the threaded member 240 and the interface portion 245 of the first drive gear 250. In the case where the distal threaded interface 264 has a higher pitch count than the interface portion 241 on the threaded member 240, the input gears can be used to rotate the second drive member to make a coarse adjustment of position, and the lead screw can be rotated to make a fine adjustment in the position of the surgical tool.

FIG. 5A is an illustration of an example second drive member 265 and an anti-rotation block. FIG. 5B shows the anti-rotation block 505 engaged in a slot in the drive system 100. The anti-rotation block 505 can be connected to the second drive member 265. A component of the drive system 100 includes a slot sized and shaped to engage the anti-rotation block 505. Because the anti-rotation block 505 is engaged with the slot 610, rotation of the drive member is prevented. As previously mentioned, the lead screw 260 can be coupled to the second drive member 265 with an engagement mechanism such as a threaded connection. When the lead screw is rotated, the rotational movement of the lead screw can be translated into axial movement of the second drive member 265 via the threaded interface. Axial movement of the drive member 265 can manipulate a surgical tool that is coupled to the second drive member 265.

FIG. 6 is a flowchart that illustrates an example method. The method can include, for example adjusting the position or configuration of a surgical instrument using a first drive system and a second drive system that are arranged in series and coupled to each other and to the surgical instrument.

At 605, the method can include driving back-drivable threads on a first drive member of the first drive system in a first direction to advance the first drive member and a second drive member of the second drive system. In an example, driving the back-drivable threads on the first drive member includes rotating a gear that has internal threads that interface with external threads on the first drive member.

The method can further include, at 610, driving back-drivable threads on the first drive member of the first drive system in a second direction to retract the first drive member and the second drive member.

The method can further include, at 615, driving threads on the second drive member to advance the second drive member, without advancing the first drive member. Step 615 can optionally include driving non back-drivable threads. In an example, driving the non-back-drivable threads on the second drive member can include rotating a lead screw that has external threads that engage internal threads on the second drive member, the second drive member being prevented from rotation, such that rotating the lead screw causes linear displacement of the second drive member relative to the lead screw.

In an example, advancing the first drive member can effectuate a first change in position or configuration of the surgical instrument, and advancing the second drive member can effectuate a second change in the position or configuration of the surgical instrument. In another example, driving the back-drivable threads on the first drive member effectuates a first operation of the surgical instrument, and driving the non-back-drivable threads on the second drive member effectuates a second operation of the surgical instrument. In an example, driving the back-drivable threads on the first drive member advances the second drive member and the surgical tool at a first forward advancement rate, and driving the non-back-drivable threads on the second drive member advances the second drive member and surgical tool at a second forward advancement rate, the second forward advancement rate being smaller than the first forward advancement rate.

The method can further include, at step 620, decoupling the second drive system from the first drive system and manually retracting a lead screw and surgical instrument.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round", a component that is not precisely circular (e.g., one that is slightly oblong or is a many-sided polygon) is still encompassed by this description.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A medical device drive system comprising:
    a support structure;
    a first drive input;
    a first drive member slidably coupled to the support structure and operatively coupled with the first drive input, the first drive member being slidable in a forward direction and a backward direction relative to the support structure, and the first drive member being drivable by the first drive input in the forward direction and in the backward direction;
    a second drive input;
    an intermediate drive member movably coupled to the first drive member and operatively coupled with the second drive input, the intermediate drive member being drivable by the second drive input;
    a second drive member operatively coupled to the intermediate drive member, the second drive member being drivable by the intermediate drive member in a forward direction; and
    a medical tool coupled to the second drive member, wherein driving the second drive member in a forward direction effectuates a change in a position or configuration of the medical tool.

2. The medical device drive system of claim 1, wherein the second drive member is not back-drivable by the intermediate drive member.

3. The medical device drive system of claim 1, wherein the first drive member and first drive input are configured to convert rotational motion of the first drive input into translational movement of the first drive member, and the intermediate drive member and second drive member are configured to convert rotational movement of the intermediate drive member into translational movement of the second drive member.

4. The medical device drive system of claim 3, wherein:
    the intermediate drive member is a lead screw, the lead screw being rotatably coupled to the first drive member; and
    the second drive input is configured to turn the lead screw.

5. The medical device drive system of claim 4, wherein the lead screw includes a threaded portion and the second drive member includes a nut having threads engaged with the threaded portion of the lead screw, the threads on the nut being forward-drivable and not back-drivable.

6. The medical device drive system of claim 5, wherein the threaded portion of the lead screw defines a lead screw axis, and the nut is slidably coupled to the support structure, the nut being slidable along the lead screw axis, the medical device drive system further comprising a nut restraining feature sized and shaped to restrict rotational movement of the nut, wherein turning the lead screw drives the nut along the lead screw axis.

7. The medical device drive system of claim 4, wherein the second drive input includes a drive gear that is coupled to the lead screw, the medical device drive system further comprising a drive input gear that is operatively coupled with the drive gear.

8. The medical device drive system of claim 7, wherein the medical tool is a surgical tool, and the drive input gear is coupled to a surgical control system.

9. The medical device drive system of claim 1, wherein:
the intermediate drive member has portions defining a longitudinal axis, and the intermediate drive member is rotatable about the longitudinal axis with respect to the first drive member, the intermediate drive member being releasably coupled to first drive member, and
the medical device drive system has a first state and a second state:
in the first state the intermediate drive member is coupled to the first drive member, and the intermediate drive member is not displaceable along the longitudinal axis, and
in the second state the intermediate drive member is not coupled to the first drive member, and the intermediate drive member, the second drive member and the medical tool are displaceable together along the longitudinal axis.

10. A method of adjusting the position or configuration of a surgical instrument using a first drive system and a second drive system that are arranged in series and coupled to each other and to the surgical instrument, the method comprising:
driving back-drivable threads on a first drive member of the first drive system in a first direction to advance the first drive member and a second drive member of the second drive system;
driving back-drivable threads on the first drive member of the first drive system in a second direction to retract the first drive member and the second drive member; and
driving non back-drivable threads on the second drive member to advance the second drive member, without advancing the first drive member;
wherein advancing the first drive member effectuates a first change in position or configuration of the surgical instrument, and advancing the second drive member effectuates a second change in the position or configuration of the surgical instrument.

11. The method of claim 10, wherein advancing the driving the back-drivable threads on the first drive member effectuates a first operation of the surgical instrument, and driving the non-back-drivable threads on the second drive member effectuates a second operation of the surgical instrument.

12. The method of claim 10, wherein driving the back-drivable threads on the first drive member advances the second drive member and the surgical tool at a first forward advancement rate, and driving the non-back-drivable threads on the second drive member advances the second drive member and surgical tool at a second forward advancement rate, the second forward advancement rate being smaller than the first forward advancement rate.

13. The method of claim 10, wherein driving the back-drivable threads on the first drive member includes rotating a gear that has internal threads that interface with external threads on the first drive member.

14. The method of claim 10, wherein driving the non-back-drivable threads on the second drive member includes rotating a lead screw that has external threads that engage internal threads on the second drive member, the second drive member being prevented from rotation, wherein rotating the lead screw causes linear displacement of the second drive member relative to the lead screw.

15. The method of claim 10, further comprising decoupling the second drive system from the first drive system and manually retracting a lead screw and surgical instrument.

\* \* \* \* \*